(12) United States Patent
Gutacker et al.

(10) Patent No.: US 10,138,329 B2
(45) Date of Patent: Nov. 27, 2018

(54) ORGANIC ZINC COMPLEXES AS CATALYSTS FOR CONDENSATION REACTIONS

(71) Applicant: Henkel AG & Co. KGaA, Duesseldorf (DE)

(72) Inventors: Andrea Gutacker, Duesseldorf (DE); Kerstin Unger, Oberhausen (DE); Johann Klein, Duesseldorf (DE); Helene Boudet, Hilden (DE); Udo Kragl, Kritzmow (DE); Henrik Lund, Rostock (DE); Esteban Mejia, Rostock (DE); Jens Baumgard, Rostock (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/652,368

(22) Filed: Jul. 18, 2017

(65) Prior Publication Data
US 2017/0313822 A1 Nov. 2, 2017

Related U.S. Application Data

(63) Continuation of application No. PCT/EP2016/051271, filed on Jan. 22, 2016.

(30) Foreign Application Priority Data

Jan. 26, 2015 (DE) .................. 10 2015 201 292

(51) Int. Cl.
| | |
|---|---|
| *C08G 77/08* | (2006.01) |
| *C07F 3/06* | (2006.01) |
| *C08L 83/04* | (2006.01) |
| *C08G 77/20* | (2006.01) |
| *C08K 5/5425* | (2006.01) |
| *C08K 5/56* | (2006.01) |

(52) U.S. Cl.
CPC ............ *C08G 77/08* (2013.01); *C07F 3/06* (2013.01); *C08G 77/20* (2013.01); *C08K 5/5425* (2013.01); *C08K 5/56* (2013.01); *C08L 83/04* (2013.01)

(58) Field of Classification Search
None
See application file for complete search history.

(56) References Cited

FOREIGN PATENT DOCUMENTS

| CN | 101723966 A | 6/2010 |
|---|---|---|
| EP | 0564253 A1 | 10/1993 |

OTHER PUBLICATIONS

Granum et al. "Synthesis and Characterization of Sterically Encumbered beta-Ketoiminate Complexes of Iron(II) and Zinc(II)" Dalton Trans., 2011, 40, 5881 (Year: 2011).*
Matthews et al. "Synthesis and characterization of zinc AP-MOCVD precursors and their utility in the growth of ZnO" Dalton Trans., 2006, 3806-3811. (Year: 2006).*
Bekermann et al. "Volatile, Monomeric, and Fluorine-Free Precursoes for the Metal Organic Chemical Vapor Deposition of Zinc Oxide" Eur. J. Inorg. Chem. 2010, 1366-1372. (Year: 2010).*
International Search Report for International PCT Patent Application No. PCT/EP2016/051271 dated May 4, 2016.
Mirela-Femanda Zaltariov et al., Synthesis, characterization and antimicrobial activity of new Cu(II) and Zn(II) complexes with Schiff bases derived from trimethylsilyl-propyl-p-aminobenzoate, Polyhedron, vol. 100, 2015, pp. 121-131.
Amir Reza Judy Azar et al., Novel magnetic nanomaterials: Synthesis, characterization and study of their catalytic application, Materials Chemistry and Physics, vol. 168, 2015, pp. 85-94.
A. G. Starikov et al., Effect of ligand environment on the mechanism of enantiomerization of BeII, ZnII, and CuII bischelate complexes, Russian Chemical Bulletin, International Edition, vol. 58, No. 3, pp. 513-521.
Esin Ispir et al., The d10 Metal Chelates Derived from Schiff Base Ligands Having Silane: Synthesis, Characterization and Antimicrobial Studies of Cadmium(II) and Zinc(II) Complexes, Synthesis and Reactivity in Inorganic, Metal-Organic, and Nano-Metal Chemistry, vol. 36, No. 8, 2006, pp. 627-631.
A. D. Garnovskii et al., Tribochemically Active Chelate Complexes of Salicylideneimines, Russian Journal of Coordination Chemistry, vol. 35, No. 2, 2009, pp. 120-127.
Kimberly A. Gerling et al., Synthesis and structures of bis-ligated zinc complexes supported by tridentate ketoimines that initiate L-lactide polymerization, Dalton Transactions, vol. 43, No. 43, 2014, pp. 16498-16508.

* cited by examiner

*Primary Examiner* — Robert S Loewe
(74) *Attorney, Agent, or Firm* — James E. Piotrowski

(57) ABSTRACT

This disclosure relates to a zinc complex formula (I), as defined herein, to the use of this zinc complex as a catalyst, in particular for the catalysis of a condensation reaction of organosilicon compounds. This disclosure also relates to preparations containing said compounds and to the use thereof.

18 Claims, No Drawings

ORGANIC ZINC COMPLEXES AS CATALYSTS FOR CONDENSATION REACTIONS

The invention relates to organic zinc compounds which are useful as catalysts for the condensation of silicon-containing polymers and polymer mixtures and which can replace the known, highly reactive organolithium compounds. The described zinc compounds are characterized by good catalytic activity and stability. The invention furthermore relates to preparations comprising these catalysts, to methods for producing functionalized polyorganosiloxanes using these zinc compounds, and to the uses thereof.

Silicone polymers, in particular polymethylsiloxanes such as polydimethylsiloxane (PDMS), are very significant as adhesives, sealants and insulating materials. Among these, those that vulcanize at low temperatures and under ambient conditions account for a significant market share. Typical formulations comprise a reactive polyorganosiloxane, which was produced by reacting a silanol-terminated polyorganosiloxane with a silane capping agent. Typically, catalysts are required for this end capping, which selectively facilitate end capping, without curing the polyorganosiloxane. Previously, primarily organic lithium compounds were used for end capping, such as the organolithium compounds disclosed in EP 0 564 253 B1, which deliver good results with respect to the curing time and selectivity. These compounds, however, are disadvantageous for stability reasons since these render the formulations unstable if not removed or decomposed in a complex process.

While a wide variety of other catalysts are known as substitutes for the known lithium compounds, such as amines, organic oxides, potassium acetate, organotitanium derivatives, titanium/amine combinations, carboxylic acid/amine combinations, and carbamates and oxime-containing organic compounds, these known alternatives often have disadvantages with respect to stability, activity or compatibility.

It is therefore an object of the present invention to provide alternatives to the organolithium compounds known as condensation agents, which overcome the known disadvantages.

The present invention achieves the object of providing improved condensation agents for the end capping of polymers that comprise reactive silanol groups (Si—OH groups), which satisfy the above-described requirements, which is to say have sufficient catalytic activity and stability and are compatible with the components used. Surprisingly, the inventors found that zinc complexes comprising ß-ketoimine ligands have the desired properties, and are thus suitable as condensation catalysts for the end capping of silanol group-terminated polymers.

In a first aspect, the invention thus relates to a zinc complex of formula (1),

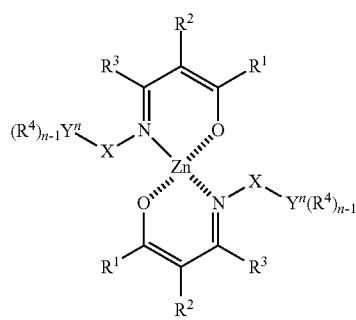

wherein
each $R^1$, $R^2$ and $R^3$, independently of one another, denotes:
  hydrogen;
  a substituted or unsubstituted alkyl, alkenyl or alkinyl functional group;
  a substituted or unsubstituted cycloaliphatic functional group or aryl functional group;
  a substituted or unsubstituted heteroalicyclic functional group or heteroaryl functional group;
  $-OR^5$, $-SR^5$, $-N(R^5)_2$, $-Si(R^5)_3$ or $-P(R^5)_3$; or
  $R^1$ and $R^2$, or $R^2$ and $R^3$, together with the carbon atoms to which they are bound, form a 5- to 8-membered substituted or unsubstituted cycloaliphatic, heteroalicyclic aryl or heteroaryl ring;
each X, independently, denotes a divalent functional group, which is selected from:
  a substituted or unsubstituted alkyl, alkenyl or alkinyl functional group;
  a substituted or unsubstituted cycloaliphatic functional group or aryl functional group;
  a substituted or unsubstituted heteroalicyclic functional group or heteroaryl functional group; or
  $-OR^5$, $-SR^5$, $-N(R^5)_2$, $-Si(R^5)_3$ and $-P(R^5)_3$;
each $Y^n$, independently, denotes C, Si, Ge, N, P, O, S, wherein n denotes the oxidation state or the valence;
each $R^4$, independently, denotes:
  hydrogen;
  a substituted or unsubstituted alkyl, alkenyl or alkinyl functional group;
  a substituted or unsubstituted cycloaliphatic functional group or aryl functional group;
  a substituted or unsubstituted heteroalicyclic functional group or heteroaryl functional group;
  $-OR^5$, $-SR^5$, $-N(R^5)_2$, $-Si(R^5)_3$ or $-P(R^5)_3$; or
  two $R^4$, together with $Y^n$, form a 5- to 8-membered substituted or unsubstituted cycloaliphatic, heteroalicyclic aryl or heteroaryl ring;
each $R^5$, independently, denotes
  hydrogen;
  a substituted or unsubstituted alkyl, alkenyl or alkinyl functional group;
  a substituted or unsubstituted cycloaliphatic functional group or aryl functional group; or
  a substituted or unsubstituted heteroalicyclic functional group or heteroaryl functional group; and
each n, independently, is an integer from 1 to 4, and in particular 2, 3 or 4.

In a further aspect, the invention relates to a composition, and in particular a catalyst composition for the polycondensation of organosilicon compounds, which comprises the zinc complexes described herein.

The invention furthermore relates to a method for producing a curable polymer, and in particular a polyorganosiloxane, comprising at least one terminal functional group bound to a silicon atom, comprising the reacting of a silanol-terminated polymer, and in particular polydiorganosiloxane, with at least one compound of formula (2)

wherein
each $R^{10}$ denotes a hydrocarbon functional group having 1 to 20 carbon atoms, or a triorganosiloxane group of formula $-O-Si(R^{13})_3$, wherein each $R^{13}$, independently, denotes a hydrocarbon functional group having 1 to 20 carbon atoms;
each $R^{11}$ denotes a functional group of formula $-(L)_n-(F)_o$, wherein L is a divalent or trivalent hydrocarbon functional group, which optionally comprises one or more heteroatoms, and in particular oxygen atoms, F is an unsaturated $C_{2-6}$ hydrocarbon functional group, halogen, a perfluorinated hydrocarbon functional group, glycidoxy, —NHR$^{14}$ or —O—C(O)—CR$^{15}$=CR$^{16}$R$^{17}$, wherein R$^{14}$ is hydrogen, C$_{1-6}$ alkyl or L-NH$_2$, R$^{15}$, R$^{16}$ and R$^{17}$, independently, are hydrogen, C$_{1-6}$ alkyl or phenyl, n is 0 or 1, and o is 1 or 2; each R$^{12}$, independently, denotes a hydroxy group or a hydrolyzable group, and in particular an oxime group and/or an alkoxy group;
k is 0, 1, 2 or 3; and
m is 0 or 1, wherein k+m=0, 1, 2 or 3, with the proviso that m is not 0 when k+m=3;
in the presence of a catalyst, wherein the catalyst comprises at least one zinc complex, as described herein.

Still another aspect relates to the curable polymer, and in particular polyorganosiloxane, which can be obtained by the method described herein, and to curable compositions comprising the same, as well as to the use thereof as an adhesive or a sealant.

Finally, the invention also relates to the use of a zinc complex, as described herein, as a catalyst, in particular to catalyze the condensation reaction of organosilicon compounds. The term "catalyst," as used herein in connection with the zinc compounds according to the invention, shall be understood to mean a compound that is able to facilitate the condensation reaction necessary for the end capping of organosilicon compounds, without curing the polymer. Catalysts that facilitate the actual curing process are referred to as "vulcanization catalysts" herein.

To the extent that the present application references molecular weights, the information refers to the weight average molecular weight, which is to say the M$_w$ value, unless indicated otherwise, and not to the arithmetic mean. The molecular weight is determined in accordance with DIN 55672-1:2007-08 by way of gel permeation chromatography (GPC) using tetrahydrofuran (THF) as the eluent, preferably at 35° C.

"At least one," as used herein, denotes 1 or more, which is to say 1, 2, 3, 4, 5, 6, 7, 8, 9, or more. With respect to an ingredient, the expression refers to the type of the ingredient and not to the absolute number of the molecules. "At least one polymer" thus, for example, denotes at least one type of polymer, which is to say that one type of polymer or a mixture of several different polymers may be used. Together with weight information, the expression refers to all compounds of the described type that are present in the composition/mixture, which is to say that, beyond the indicated amounts of the corresponding compounds, the composition does not include any further compounds of this type.

All percentage information provided in connection with the compositions described herein refers to wt. %, in each case based on the mixture in question, unless explicitly indicated otherwise.

In the compounds of formula (1), each R$^1$, R$^2$ and R$^3$, independently of one another, denotes:
hydrogen;
a substituted or unsubstituted alkyl, alkenyl or alkinyl functional group, in particular having 1 to 10 carbon atoms;
a substituted or unsubstituted cycloaliphatic functional group or aryl functional group, in particular having 6 to 10 carbon atoms;
a substituted or unsubstituted, in particular 5- to 6-membered heteroalicyclic functional group or heteroaryl functional group, in particular having 3 to 10 carbon atoms and 1 to 4 heteroatoms, selected from O, S and N;
—OR$^5$, —SR$^5$, —N(R$^5$)$_2$, —Si(R$^5$)$_3$ or —P(R$^5$)$_3$; or
R$^1$ and R$^2$, or R$^2$ and R$^3$, together with the carbon atoms to which they are bound, form a 5- to 8-membered substituted or unsubstituted cycloaliphatic, heteroalicyclic aryl or heteroaryl ring.

"Alkyl," as used herein, refers to a saturated aliphatic hydrocarbon, including straight-chain and branched groups. The alkyl group preferably comprises 1 to 10 carbon atoms (when a numerical range, such as "1 to 10" is indicated herein, this shall mean that this group, which in the present case is the alkyl group, can comprise 1 carbon atom, 2 carbon atoms, 3 carbon atoms and the like, up to and including 10 carbon atoms). In particular, the alkyl can be an intermediate alkyl having 1 to 6 carbon atoms, or a lower alkyl having 1 to 4 carbon atoms, such as methyl, ethyl, n-propyl, isopropyl, butyl, iso-butyl, tert-butyl and the like. The alkyl functional groups can be substituted or unsubstituted. "Substituted," as used in the present context, shall be understood to mean that one or more carbon atoms and/or hydrogen atoms of the alkyl functional group are replaced with heteroatoms or functional groups. Substituting one or more carbon atoms with heteroatoms yields heteroalkyl groups, in which one or more carbon atoms are replaced with heteroatoms, in particular selected from O, S, N and Si. Examples of such heteroalkyl groups include, without being limited to these, methoxymethyl, ethoxyethyl, propoxypropyl, methoxyethyl, isopentoxypropyl, ethylaminoethyl, trimethoxypropylsilyl, and the like. Functional groups that can substitute hydrogen atoms are, in particular, selected from =O, =S, —OH, —SH, —NH$_2$, —NO$_2$, —CN, —F, —Cl, —Br, —I, —OCN, —NCO, C$_{3-8}$ cycloalkyl, C$_{6-14}$ aryl, a 5- to 10-membered heteroaryl ring, in which 1 to 4 ring atoms, independently of one another, are nitrogen, oxygen or sulfur, and a 5- to 10-membered heteroalicyclic ring, in which 1 to 3 ring atoms, independently of one another, are nitrogen, oxygen or sulfur.

"Alkenyl," as used herein, refers to an alkyl group, as defined herein, which comprises at least two carbon atoms and at least one carbon-carbon double bond, such as ethenyl, propenyl, butenyl or pentenyl and the structural isomers thereof, such as 1- or 2-propenyl, 1-, 2- or 3-butenyl, and the like. Alkenyl groups may be substituted or unsubstituted. If they are substituted, the substituents are as defined above for alkyl.

"Alkinyl," as used herein, refers to an alkyl group, as defined herein, which comprises at least two carbon atoms and at least one carbon-carbon triple bond, such as ethinyl (acetylene), propinyl, butinyl or petinyl and the structural isomers thereof, as described above. Alkinyl groups may be substituted or unsubstituted. If they are substituted, the substituents are as defined above for alkyl.

A "cycloaliphatic functional group" or "cycloalkyl group," as used herein, refers to monocyclic or polycyclic (multiple rings that comprise shared carbon atoms) groups, and in particular comprising 3 to 8 carbon atoms, in which the ring does not have a complete conjugated pi electron system, such as cyclopropyl, cyclobutyl, cyclopentyl, cyclohexyl, cyclobutenyl, cyclopentenyl, cyclohexenyl, and the like. Cycloalkyl groups may be substituted or unsubstituted. "Substituted," as used in the present context, shall be understood to mean that one or more hydrogen atoms of the cycloalkyl group are replaced with functional groups. Functional groups that can substitute hydrogen atoms are, in particular, selected from =O, =S, —OH, —SH, —NH$_2$, —NO$_2$, —CN, —F, —Cl, —Br, —I, —OCN, —NCO, C$_{1-10}$ alkyl, C$_{2-10}$ alkenyl, C$_{2-10}$ alkinyl, C$_{3-8}$ cycloalkyl, C$_{6-14}$ aryl, a 5- to 10-membered heteroaryl ring, in which 1 to 4 ring atoms, independently of one another, are nitrogen, oxygen or sulfur, and a 5- to 10-membered heteroalicyclic ring, in which 1 to 3 ring atoms, independently of one another, are nitrogen, oxygen or sulfur.

"Aryl," as used herein, refers to monocyclic or polycyclic groups (which is to say rings that share adjacent pairs of carbon atoms), in particular comprising 6 to 14 carbon ring atoms, which have a complete conjugated pi electron system. Examples of aryl groups are phenyl, naphthalinyl and anthracenyl. Aryl groups may be substituted or unsubstituted. If they are substituted, the substituents are as defined above for cycloalkyl.

A "heteroaryl" group, as used herein, refers to a monocyclic or polycyclic (which is to say rings that share an adjacent pair of ring atoms) aromatic ring, comprising in particular 5 to 10 ring atoms, wherein one, two, three or four ring atoms are nitrogen, oxygen or sulfur, and the remainder is carbon. Examples of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, pyridinyl, pyrimidinyl, carbazolyl, xanthenyl or benzoquinolyl. Heteroaryl groups may be substituted or unsubstituted. If they are substituted, the substituents are as defined above for cycloalkyl.

A "heteroalicyclic functional group" or a "heterocycloalkyl group," as used herein, refers to a monocyclic or fused ring composed of 5 to 10 ring atoms, which comprises one, two or three heteroatoms selected from N, O and S, wherein the remainder of the ring atoms is carbon. A "heterocycloalkenyl" group additionally comprises one or more double bonds. The ring, however, does not have a complete conjugated pi electron system. Examples of heteroalicyclic groups are pyrrolidine, piperidine, piperazine, morpholine, imidazolidine, tetrahydropyridazine, tetrahydrofuran, thiomorpholine, tetrahydropyridine, and the like. Heterocycloalkyl groups may be substituted or unsubstituted. If they are substituted, the substituents are as defined above for cycloalkyl.

In various embodiments of the invention, $R^1$, $R^2$ and $R^3$, independently of one another, are selected from hydrogen and a substituted or unsubstituted alkyl functional group. The alkyl functional group is, in particular, an unsubstituted $C_{1-4}$ alkyl functional group, and preferably methyl or ethyl. In especially particularly preferred embodiments, $R^1$ and $R^3$ are methyl, and $R^2$ is hydrogen. Such ligands can be achieved by reacting a primary amine with acetylacetone, as is described in detail hereafter.

In various embodiments, $R^1$ and $R^2$, or $R^2$ and $R^3$, together with the carbon atoms to which they are bound, can form a 5- to 6-membered substituted or unsubstituted cycloaliphatic, heteroalicyclic aryl or heteroaryl ring, and in particular a cycloaliphatic or heteroalicyclic ring.

In the compounds of formula (1), each X, independently, denotes a divalent functional group, which is selected from:
a substituted or unsubstituted alkyl, alkenyl or alkinyl functional group;
a substituted or unsubstituted cycloaliphatic functional group or aryl functional group;
a substituted or unsubstituted heteroalicyclic functional group or heteroaryl functional group; or
$-OR^5$, $-SR^5$, $-N(R^5)_2$, $-Si(R^5)_3$ and $-P(R^5)_3$.

"Divalent," as used in the present context, shall be understood to mean that the functional group X comprises two free bonds, with which it is bound to $-Y''(R^4)_{n-1}$ or $-N=C(R^3)-C(R^2)=C(R^1)-O$, such as methylidenyl, phenylidenyl, and the like.

In various embodiments of the invention, X is an alkyl functional group of formula $-(CHR')_p-$, wherein each R' is H or a $C_{1-4}$ alkyl functional group, and p is an integer from 1 to 10, in particular 1 to 6, still more preferably 1 to 3. In certain embodiments, X is an alkyl functional group of formula $-(CH_2)_p-$, wherein p is an integer from 1 to 6, and in particular 3.

In the compounds of formula (1), each $Y''$, independently, denotes C, Si, Ge, N, P, O, S, wherein n denotes the oxidation state or the valence. "Oxidation state" or "valence," as used in the context with Y, refers to the bonds that Y can form. For example, C and Si have valences of 4, while O and S each have a valence of 2. Ge has a valence of 2 or 4, and N and P have valences of 3 or 5. In various embodiments of the invention, each n, independently, is thus an integer from 1 to 4, and in particular 2, 3 or 4.

In various embodiments of the invention, $Y''$ is C, Si or O, in particular C or Si, and still more preferably Si.

In the compounds of formula (1), each $R^4$, independently, is:
hydrogen;
a substituted or unsubstituted alkyl, alkenyl or alkinyl functional group;
a substituted or unsubstituted cycloaliphatic functional group or aryl functional group;
a substituted or unsubstituted heteroalicyclic functional group or heteroaryl functional group;
$-OR^5$, $-SR^5$, $-N(R^5)_2$, $-Si(R^5)_3$ or $-P(R^5)_3$; or
two $R^4$, together with $Y''$, form a 5- to 8-membered substituted or unsubstituted cycloaliphatic, heteroalicyclic aryl or heteroaryl ring;
with the proviso that
(1) when $Y''$ is O or S, $R^4$ is not $-OR^5$, $-SR^5$ or $-N(R^5)_2$;
(2) when $Y''$ is Si, Ge or P, $R^4$ is not H, $Si(R^5)_3$ or $-P(R^5)_3$.

In various embodiments, $R^4$ is selected from the group consisting of a substituted or unsubstituted alkyl functional group, in particular having 1 to 10 carbon atoms, and $-OR^5$.

In the compounds of formula (1), each $R^5$, independently, is:
hydrogen;
a substituted or unsubstituted alkyl, alkenyl or alkinyl functional group;
a substituted or unsubstituted cycloaliphatic functional group or aryl functional group; or
a substituted or unsubstituted heteroalicyclic functional group or heteroaryl functional group.

In various embodiments of the invention, the functional group $-Y''(R^4)_{n-1}$ is selected from silyl groups, and in particular dialkylalkoxysilyl, alkyldialkoxysilyl, trialkoxysilyl or trialkylsilyl, wherein alkyl or alkoxy are $C_{1-4}$ alkyl or alkoxy. Triethyoxysilyl and trimethoxysilyl are especially particularly preferred.

The zinc complexes of formula (1) can be achieved by reacting diorganozinc compounds, such as, in particular, diethylzinc, with two equivalents of the ligand of formula (3),

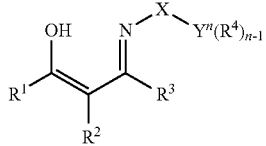

(3)

wherein $R^1$ to $R^4$, $Y^n$ and n are as defined above, in a suitable solvent under protective gas and in the absence of water at room temperature.

The ligands of formula (3) can be achieved by reacting 1,3-dicarbonyl compounds of formula (4), and in particular acetylacetone, with primary amines of formula (5)

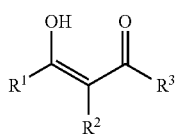

(4)

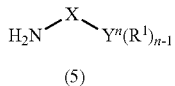

(5)

wherein $R^1$ to $R^4$, $Y^n$ and n are as defined above, for example as described in Lee et al. (Adv. Synth. Catal. 2009, 351, 2912-20) and Jin & Lee (Angew. Chem. Int. Ed. 2010, 49, 1119-1122).

In a further aspect, the invention relates to compositions comprising the zinc complexes according to the invention. These compositions can be catalyst compositions, for example. These can comprise the zinc compounds, as described herein, for example in combination with further active ingredients or auxiliaries, such as solvents.

The zinc compounds of formula (1) described herein are suitable, in particular, as catalysts for the functionalization of organopolysiloxanes comprising terminal silanol groups with alkoxysilanes that carry one or more functional groups, which is to say the so-called end capping.

Under standard conditions (25° C., 1013 mbar), the described zinc compounds are liquid compounds and, as a result, they are superior to the previously used solid catalysts in terms of activity and efficiency.

In various embodiments, the invention thus also relates to a method for producing a curable polymer, and in particular a polyorganosiloxane, comprising at least one terminal functional group bound to a silicon atom, comprising the reacting of a silanol-terminated polymer, and in particular polydiorganosiloxane, with at least one compound of formula (2)

$$(R^{10})_k(R^{11})_m Si(R^{12})_{4-(k+m)}$$ (2), wherein
each $R^{10}$ denotes a hydrocarbon functional group having 1 to 20 carbon atoms, or a triorganosiloxane group of formula —O—Si$(R^{13})_3$, wherein each $R^{13}$, independently, denotes a hydrocarbon functional group having 1 to 20 carbon atoms; each $R^{11}$ denotes a functional group of formula -(L)$_n$-(F)$_o$, wherein L is a divalent or trivalent hydrocarbon functional group, which optionally comprises one or more heteroatoms, and in particular oxygen atoms, F is an unsaturated $C_{2-6}$ hydrocarbon functional group, halogen, a perfluorinated hydrocarbon functional group, glycidoxy, —NHR$^{14}$ or —O—C(O)—CR$^{15}$=CR$^{16}$R$^{17}$, wherein R$^{14}$ is hydrogen, $C_{1-6}$ alkyl or L-NH$_2$, R$^{15}$, R$^{16}$ and R$^{17}$, independently, are hydrogen, $C_{1-6}$ alkyl or phenyl, n is 0 or 1, and o is 1 or 2; each $R^{12}$, independently, denotes a hydroxy group or a hydrolyzable group, and in particular an oxime group and/or an alkoxy group;
k is 0, 1, 2 or 3; and
m is 0 or 1, wherein k+m=0, 1, 2 or 3, with the proviso that m is not 0 when k+m=3;
in the presence of a catalyst, wherein the catalyst comprises at least one zinc complex as defined herein.

The curable polymer is preferably a moisture-curable polymer. The curable polymer, which can be produced by way of the methods according to the invention, preferably comprises terminal alkoxysilyl groups. These can optionally be combined with vinyl functionalities, and preferably acrylate functionalities or epoxy functionalities, so as to allow double photocrosslinking and moisture crosslinking. One such example is the reaction product of vinyltrimethoxysilane with a polydimethylsiloxane comprising terminal silanol in the presence of a catalytic amount of the zinc catalysts described herein.

There are no particular restrictions with respect to the polymer backbone of the curable polymer, and all known polymers having different types of backbones may be used. In various embodiments, the polymer is thus selected from alkyd resins, (meth)acrylates and (meth)acrylamides, and the salts thereof, phenolic resins, polyalkylenes, polyamides, polycarbonates, polyols, polyethers, polyesters, polyurethanes, vinyl polymers, siloxanes, and copolymers consisting of at least two of the aforementioned polymer classes.

Particularly preferably, however, siloxanes are used, in particular polydiorganosiloxanes, and still more preferably polydimethylsiloxanes (PDMS).

The aforementioned materials are thereafter cured by way of moisture crosslinking or double moisture crosslinking and photocrosslinking.

So as to produce a curable polymer comprising terminal alkoxysilyl, and optionally vinyl or acrylate functionality, a silanol-terminated polymer is reacted with a silane, which comprises at least two alkoxy groups, and optionally additionally at least one epoxy, vinyl or acrylate group, in the presence of a catalytic amount of the zinc compounds described herein, wherein the silane is linked to the terminal silanol group by way of a condensation reaction between the hydroxyl group and an alkoxy group, whereby a curable polymer comprising terminal alkoxysilyl, and optionally epoxy, vinyl or acrylate functionality, is obtained.

The silanol-terminated polymer comprises at least one terminal silanol group, and preferably at least two terminal silanol groups. In the case of branched polymers, the polymer preferably comprises a silanol group at each end. "Silanol group," as used herein, refers to the Si—OH group, which is to say a hydroxyl group that is bound directly to a silicon atom.

In the compounds of formula (2), $R^{10}$ in the various embodiments is selected from methyl, ethyl and phenyl, and in particular methyl.

In various embodiments, $R^{11}$ is selected from:
—CH=CH$_2$, —CH$_2$—Cl, —(CH$_2$)$_3$—Cl, —CH$_2$—O—C(O)—CH=CH$_2$, —CH$_2$—O—C(CH$_3$)=CH$_2$, —(CH$_2$)$_3$—O—C(O)—CH=CH$_2$, —(CH$_2$)$_3$—O—C(O)—C(CH$_3$)=CH$_2$, —(CH$_2$)$_2$-phenyl-CH=CH$_2$, —CH(CH$_3$)-phenyl-CH=CH$_2$, —(CH$_2$)$_2$-phenyl-CH$_2$—Cl, —CH(CH$_3$)-phenyl-CH$_2$—Cl, —(CH$_2$)$_3$—NH$_2$, —(CH$_2$)$_3$—NH—(CH$_2$)$_2$—NH$_2$ and —(CH$_2$)$_3$—SH.

In various embodiments, $R^{12}$ is selected from methoxy and ethoxy. However, $R^{12}$ can also be an oxime group.

"Oxime groups," as used herein, include ketoximes and aldoximes and generally denote groups that comprise the functional group $R'_2C=N—O—$, wherein the oxygen atom is bound to the silicon atom, and R' can be H or any other group, preferably an alkyl group.

In various embodiments, k is 0, 1 or 2, m is 0 or 1, and k+m=0, 1 or 2.

In preferred embodiments, $R^{10}$ denotes methyl, ethyl or phenyl, and in particular methyl, and $R^{11}$ denotes a group selected from:
—CH=CH$_2$, —CH$_2$—Cl, —(CH$_2$)$_3$—Cl, —CH$_2$—O—C(O)—CH=CH$_2$, —CH$_2$—O—C(CH$_3$)=CH$_2$, —(CH$_2$)$_3$—O—C(O)—CH=CH$_2$, —(CH$_2$)$_3$—O—C(O)—C(CH$_3$)=CH$_2$, —(CH$_2$)$_2$-phenyl-CH=CH$_2$, —CH(CH$_3$)-phenyl-CH=CH$_2$, —(CH$_2$)$_2$-phenyl-CH$_2$—Cl, —CH(CH$_3$)-phenyl-CH$_2$—Cl, —(CH$_2$)$_3$—NH$_2$, —(CH$_2$)$_2$—NH—(CH$_2$)$_2$—NH$_2$ and —(CH$_2$)$_3$—SH; $R^{12}$ is selected from methoxy and ethoxy; k is 0, 1 or 2, m is 0 or 1, and k+m=0, 1 or 2.

The compound of formula (2) is thus, for example, selected from: tetramethoxysilane, tetraethoxysilane, tetrapropoxysilane, methyltrimethoxysilane, methyltriethoxysilane, propyltrimethoxysilane, propyltriethoxysilane, phenyltrimethoxysilane, phenyltriethoxysilane, vinyltrimethoxysilane, vinyltriethoxysilane, 3-chloropropyltrimethoxysilane, [2-(o,m,p-chloromethylphenyl)ethyl]trimethoxysilane and mixtures thereof, [1-(o,m,p-chloromethylphenyl)ethyl]trimethoxysilane and mixtures thereof, 3-aminopropyltrimethoxysilane, 3-aminopropyltriethoxysilane, [3-(2-aminoethyl)aminopropyl]trimethoxysilane, 3-mercaptopropyltrimethoxysilane, 3-methacryloxypropyltrimethoxysilane, 3-acryloxypropyltrimethoxysilane, 3-glycidoxypropyltriethoxysilane, 3-glycidoxypropyltrimethoxysilane, and mixtures thereof.

In the described methods, the compound of formula (2) is used, in particular, in an amount that ensures that essentially all terminal silanol groups are capped. This means, the compound is usually used in amounts so that the molar ratio of the compound of formula (2) to terminal silanol groups is at least 1:1, and preferably 1:1 to 1.5:1.

In the methods, the silanol-terminated polymer is typically used in amounts of 30 to 90 wt. %, the compound of formula (2) (crosslinking agent) in amounts of 2.5 to 7 wt. %, and the zinc catalyst in amounts of 0.001 to 1 wt. %.

The curable polymers obtainable by way of the described methods, which are also the subject matter of the invention, can then be formulated into a moisture crosslinkable composition, which usually additionally comprises at least one moisture crosslinking catalyst (vulcanization catalyst), such as organic tin or titanium compounds, or an amine catalyst, and optionally different additives and auxiliaries. A further subject matter of the present invention is thus also a preparation comprising the curable composition according to the invention. According to a further preferred embodiment of the preparation according to the invention, this furthermore comprises at least one compound selected from the group consisting of plasticizers, stabilizers, antioxidants, fillers, reactive diluents, desiccants, adhesion promoters, UV stabilizers, rheological auxiliaries and/or solvents. In such preparations, the amount of the reactive, curable polymer a) can be 30 to 90 wt. %, based on the total weight of the preparation. The amount of crosslinking catalyst c) can be 2.5 to 7 wt. %, based on the total weight of the preparation. Adhesion promoters can be used, for example, in amounts of 0 to 5 wt. %, based on the total weight of the preparation.

To be curable, the polymer comprises terminal silicon-containing groups, in which a hydrolyzable group is bound to the silicon atom and which is able to crosslink by forming a siloxane bond. This crosslinking reaction can be accelerated by a moisture crosslinking catalyst. In particular, the hydrolyzable group of the curable polymer is, as described above, an alkoxy group, optionally in combination with an epoxy, vinyl or (meth)acrylate group.

The curable compositions and preparations described herein can be used as adhesives and sealants. Such a use likewise forms an integral part of the invention.

It is conceivable that the viscosity of the adhesive or sealant according to the invention is too high for certain applications. This can generally be reduced and adjusted in a simple manner by using a reactive diluent, without resulting in segregation phenomena (such as migration of the plasticizer) in the cured compound.

The reactive diluent preferably comprises at least one functional group, which after the application reacts with moisture or atmospheric oxygen, for example. Examples of such groups are silyl groups, isocyanate groups, vinyl unsaturated groups and polyunsaturated systems.

All compounds that can be mixed with the adhesive or sealant, reducing the viscosity, and that comprise at least one group reactive with the binder can be used as reactive diluents.

The viscosity of the reactive diluent is preferably less than 20,000 mPas, particularly preferably approximately 0.1 to 6000 mPas, and especially particularly preferably 1 to 1000 mPas (Brookfield RVT, 23° C., spindle 7, 10 rpm).

For example, the following substances can be used as reactive diluents: polyalkylene glycols reacted with isocyanatosilanes (such as Synalox 100-50B, DOW), carbamato propyltrimethoxysilane, alkyltrimethoxysilane, alkyltriethoxysilane, such as methyltrimethoxysilane, methyltriethoxysilane and vinyltrimethoxysilane (XL 10, Wacker), vinyltriethoxysilane, phenyltrimethoxysilane, phenyltriethoxysilane, octyltrimethoxysilane, tetraethoxysilane, vinyldimethoxymethylsilane (XL12, Wacker), vinyltriethoxysilane (GF56, Wacker), vinyltriacetoxysilane (GF62, Wacker), isooctyltrimethoxysilane (IO Trimethoxy), isooctyltriethoxysilane (IO Triethoxy, Wacker), N-trimethoxysilylmethyl-O-methylcarbamate (XL63, Wacker), N-dimethoxy(methy)silylmethyl-O-methyl-carbamate (XL65, Wacker), hexadecyltrimethoxysilane, 3-octanoylthio-1-propyltriethoxysilane, and partial hydrolysates of these compounds.

Furthermore, the following polymers from Kaneka Corp. can likewise be used as reactive diluents: MS S203H, MS S303H, MS SAT 010, and MS SAX 350.

Likewise, silane-modified polyethers can be used, which are derived, for example, from the reaction of isocyanatosilanes with Synalox types.

Additionally, polymers that can be produced from an organic skeleton by way of grafting with a vinyl silane or reacting with polyol, polyisocyanate and alkoxysilane can be used as reactive diluents.

A polyol is understood to mean a compound that can comprise one or more OH groups in the molecule. The OH groups can be primary or secondary.

Suitable aliphatic alcohols include, for example, ethylene glycol, propylene glycol, and higher glycols, as well as other polyfunctional alcohols. The polyols can additionally comprise further functional groups, such as esters, carbonates, and amides.

To produce the preferred reactive diluents according to the invention, the corresponding polyol component is reacted with an at least difunctional isocyanate. In principle, the at least difunctional isocyanate used can be any isocyanate comprising at least two isocyanate groups; generally, however, compounds comprising two to four isocyanate groups, and in particular comprising two isocyanate groups, are preferred within the scope of the present invention.

The compound present as the reactive diluent within the scope of the present invention preferably comprises at least one alkoxysilyl group, wherein dialkoxysilyl and trialkoxysilyl groups are preferred among the alkoxysilyl groups.

Polyisocyanates suitable for producing a reactive diluent are, for example, ethylene diisocyanate, 1,4-tetramethylene diisocyanate, 1,4-tetramethoxybutane diisocyanate, 1,6-hexamethylene diisocyanate (HDI), cyclobutane-1,3-diisocyanate, cyclohexane-1,3- and -1,4-diisocyanate, bis(2-isocyanato-ethyl)fumarate, and mixtures of two or more of these, 1-isocyanato-3,3,5-trimethyl-5-isocyanatomethyl cyclohexane (isophorone diisocyanate, IPDI), 2,4- and 2,6-hexahydrotoluylene diisocyanate, hexahydro-1,3- or -1,4-phenylene diisocyanate, benzidine diisocyanate, naphthalene-1,5-diisocyanate, 1,6-d iisocyanato-2,2,4-trimethylhexane, 1,6-diisocyanato-2,4,4-trimethylhexane, xylylene diisocyanate (XDI), tetramethylxylylene diisocyanate (TMXDI), 1,3- and 1,4-phenylene diisocyanate, 2,4- or 2,6-toluylene diisocyanate (TDI), 2,4'-diphenylmethane diisocyanate, 2,2'-diphenylmethane diisocyanate or 4,4'-diphenylmethane diisocyanate (MDI) or the partially or fully hydrogenated cycloalkyl derivates thereof, such as fully hydrogenated MDI (H12-MDI), alkyl-substituted diphenylmethane diisocyanates, such as mono-, di-, tri- or tetraalkyldiphenylmethane diisocyanate and the partially or fully hydrogenated cycloalkyl derivates thereof, 4,4'-diisocyanatophenylperfluoroethane, phthalic acid-bis-isocyanatoethyl ester, 1-chloromethylphenyl-2,4 or -2,6 diisocyanate, 1-bromomethylphenyl-2,4 or -2,6 diisocyanate, 3,3-bis-chloromethylether-4,4'-diphenyl diisocyanate, sulfurous diisocyanates, as they can be obtained by reacting 2 moles diisocyanate with 1 mole thiodiglycol or dihydroxydihexyl sulfide, the diisocyanates and triisocyanates of dimer and trimer fatty acids, or mixtures of two or more of the aforementioned diisocyanates.

Trivalent or higher valent isocyanates, such as those obtainable, for example, by the oligomerization of diisocyanates, and in particular by the oligomerization of the abovementioned isocyanates, can likewise be used as polyisocyanates. Examples of such trivalent and higher valent polyisocyanates are the triisocyanurates of HDI or IPDI, or the mixtures thereof, or the mixed triisocyanurates thereof, and polyphenylmethylene polyisocyanate, as it can be obtained by the phosgenation of aniline formaldehyde condensation products.

In addition to, or instead of, a reactive diluent, it is also possible to use solvents and/or plasticizers to reduce the viscosity of the preparation according to the invention.

Aliphatic or aromatic hydrocarbons, halogenated hydrocarbons, ketones, ethers, esters, ester alcohols, keto alcohols, keto ethers, keto esters and ether esters are suitable solvents.

The preparation described herein can furthermore comprise hydrophilic plasticizers. These are used to improve the absorption of moisture, and thus to improve reactivity at low temperatures. Suitable plasticizers are, for example, esters of abietic acid, adipic acid esters, azelaic acid esters, benzoic acid esters, butyric acid esters, acetic acid esters, esters of higher fatty acids having approximately 8 to approximately 44 carbon atoms, epoxidized fatty acids, fatty acid esters and fats, glycolic acid esters, phosphoric acid esters, phthalic acid esters, linear or branched alcohols comprising 1 to 12 carbon atoms, propionic acid esters, sebacic acid esters, sulfonic acid esters, thiobutyric acid esters, trimellitic acid esters, citric acid esters, and nitrocellulose-based and polyvinyl acetate-based esters, and mixtures of two or more of these.

From among the phthalic acid esters, for example, dioctyl phthalate, dibutyl phthalate, diisoundecyl phthalate or butylbenzyl phthalate are suited, and dioctyl adipate, diisodecyl adipate, diisodecyl succinate, dibutyl sebacate or butyl oleate are suited from among the adipates.

The pure or mixed ethers of monofunctional, linear or branched $C_{4-16}$ alcohols or mixtures of two or more different ethers of such alcohols, are likewise suitable plasticizers, such as dioctyl ether (available as Cetiol OE from Cognis Deutschland GmbH, Düsseldorf).

End-capped polyethylene glycols are also suitable plasticizers. For example, polyethylene- or polypropylene glycol-di-$C_{1-4}$-alkyl ethers, and in particular the dimethyl or diethyl ethers of diethylene glycol or dipropylene glycol, and mixtures of two or more of these.

Particularly preferred plasticizers, however, are end-capped polyethylene glycols, such as polyethylene or polypropylene glycol dialkyl ethers, wherein the alkyl functional group has one to four carbon atoms, and in particular the dimethyl and diethyl ethers of diethylene glycol and dipropylene glycol. Acceptable curing is also achieved, in particular, with dimethyl diethylene glycol, even under unfavorable application conditions (low humidity, low temperature). Reference is made to the relevant literature of chemical engineering for further details on plasticizers.

Suitable plasticizers within the scope of the present invention are also diurethanes, which can be produced, for example, by reacting diols having OH terminal groups with monofunctional isocyanates by selecting the stoichiometry in such a way that essentially all free OH groups react. Possibly excess isocyanate can subsequently be removed from the reaction mixture, for example by distillation. A further method for producing diurethanes is to react monofunctional alcohols with diisocyanates, wherein preferably all NCO groups react.

The preparation described herein can moreover comprise up to approximately 20 wt. % customary adhesion promoters (tackifiers). Suitable adhesion promoters are, for example, resins, terpene oligomers, coumarone/indene resins, aliphatic petrochemical resins, and modified phenolic resins. Within the scope of the present invention, for example, hydrocarbon resins are suited, such as those obtained by the polymerization of terpenes, primarily α- or ß-pinene, dipentene or limonene. The polymerization of these monomers generally takes place cationically by being initiated with Friedel-Crafts catalysts. The terpene resins also include, for example, copolymers of terpenes and other monomers, such as styrene, α-methylstyrene, isoprene and the like. The aforementioned resins are used as adhesion promoters for pressure-sensitive adhesives and coating materials, for example. Likewise suitable are the terpene phenolic resins, which are produced by the acid-catalyzed addition of phenols to terpenes or colophony. Terpene phenolic resins are soluble in most organic solvents and oils and can be mixed with other resins, waxes and rubber. Within the scope of the present invention, the colophony resins and derivatives thereof, such as the esters thereof, are likewise suitable additives within the meaning described above.

Furthermore, the preparation described herein can also comprise up to approximately 7 wt. %, and in particular up to approximately 5 wt. %, antioxidants.

The preparation described herein can comprise up to approximately 2 wt. %, and preferably approximately 1 wt. %, UV stabilizers. Particularly suitable UV stabilizers are those known as hindered amine light stabilizers (HALS). It is preferred within the scope of the present invention if a UV stabilizer is used which carries a silyl group and which is introduced into the end product during crosslinking or curing. The products Lowilite 75 and Lowilite 77 (Great Lakes, USA) are particularly suitable for this purpose. Furthermore, benzotriazoles, benzophenones, benzoates, cyanoacrylates, acrylates, sterically hindered phenols, phosphorus and/or sulfur can also be added.

Frequently, it is useful to further stabilize the preparations according to the invention against penetrating moisture by using desiccants, so as to increase the shelf life even further.

Such an improvement in the shelf life can be achieved, for example, by the use of desiccants. All compounds that react with water, forming a group that is inert to the reactive groups present in the preparation, and in the process undergo preferably few changes to the molecular weight thereof, are suitable desiccants. Furthermore, the reactivity of the desiccant with respect to moisture that has penetrated into the preparation must be higher than the reactivity of the groups of the silyl group-carrying polymer according to the invention present in the preparation.

Suitable desiccants are isocyanates, for example.

Advantageously, silanes are used as desiccants. For example, vinyl silanes such as 3-vinylpropyltriethoxy silane, oxime silanes such as methyl-O,O',O''-butane-2-one-trioximosilane or O, O', O'', O'''-butane-2-one-tetraoximosilane (CAS nos. 022984-54-9 and 034206-40-1) or benzamido silanes such as bis(N-methylbenzamido)methylethoxysilane (CAS no. 16230-35-6) or carbamato silanes such as carbamatomethyltrimethoxysilane. However, the use of methyltrimethoxysilane, ethyltrimethoxysilane or vinyltrimethoxysilane, tetramethyloxysilane or tetraethylethoxysilane is possible. Vinyltrimethoxysilane and tetraethoxysilane are particularly preferred here with respect to efficiency and cost.

The above-mentioned reactive diluents are likewise suitable desiccants here, provided they have a molecular weight (Mn) of less than 5,000 g/mol and comprise terminal groups having at least the same level of reactivity with respect to penetrated moisture as, and preferably a higher level of reactivity with respect to penetrated moisture than, the reactivity of the reactive groups of the silyl group-carrying polymer according to the invention.

Finally, it is also possible to use alkyl orthoformates or orthoacetates as desiccants, such as methyl or ethyl orthoformate and methyl or ethyl orthoacetate.

The adhesives and sealants according to the invention generally comprise approximately 0 to approximately 6 wt. % desiccant.

The preparation described herein can additionally comprise fillers. For example, chalk, lime powder, precipitated and/or fumed silica, zeolites, bentonites, magnesium carbonate, diatomaceous earth, alumina, clay, tallow, titanium oxide, iron oxide, zinc oxide, sand, quartz, flint, mica, glass powder and other ground minerals are suitable for this purpose. Furthermore, it is also possible to use organic fillers, in particular carbon black, graphite, wood fibers, saw dust, wood shavings, cellulose, cotton, pulp, cotton, wood chips, chopped straw and chaff. Furthermore, it is also possible to add short fibers, such as glass fibers, glass filament, polyacrylonitrile, carbon fibers, Kevlar fibers, or polyethylene fibers. Aluminum powder is also a suitable filler.

The fumed and/or precipitated silica advantageously have a BET surface area of 10 to 90 m$^2$/g. If these are used, they do not cause any additional increase in the viscosity of the preparation according to the invention, but do contribute to strengthening of the cured preparation.

It is likewise conceivable to use fumed and/or precipitated silica having a higher BET surface area, advantageously 100 to 250 m$^2$/g, and in particular 110 to 170 m$^2$/g, as the filler. Due to the higher BET surface area, the same effect, such as strengthening of the cured preparation, can be achieved when using a lower percent by weight of silica. In this way, it is possible to use further substances so as to improve the preparation described herein with respect to other requirements.

Furthermore, hollow spheres having a mineral shell or a plastic shell are suitable fillers. These may be hollow glass spheres, for example, which are commercially available under the trade names Glass Bubbles®. Plastic-based hollow spheres, such as Expancel® or Dualite®, are described in EP 0 520 426 B1, for example. These are composed of inorganic or organic substances, each having a diameter of 1 mm or less, and preferably of 500 µm or less.

For some applications, fillers that impart thixotropy to the preparations are preferred. Such fillers are also referred to as rheological aids, for example hydrogenated castor oil, fatty acid amides or swellable plastics, such as PVC. So as to be easily pressable out of a suitable metering device (such as a tube), such preparations have a viscosity of 3,000 to 15,000, preferably of 40,000 to 80,000 mPas, or 50,000 to 60,000 mPas.

The fillers are preferably used in an amount of 1 to 80 wt. %, based on the total weight of the preparation.

The preparation is produced in accordance with known methods by thoroughly mixing the components in suitable dispersers, such as a high-shear mixer.

The composition or preparation can be used as an adhesive, a sealing compound or a knifing filler and to produce molded parts. A further field of application of the compositions is the use as a dowel, hole or crack knifing filler.

The compositions and preparations are thus suitable for adhesively bonding plastic materials, metals, glass, ceramic material, wood, derived timer products, paper, paper-based materials, rubber and textiles, for adhesively bonding flooring, for sealing building parts, windows, wall and floor covers, and joints in general. The materials can each be adhesively bonded to themselves or arbitrarily among one another.

The following examples are intended to describe the invention, without the invention being limited to these.

EXAMPLES

Example 1: Production of the Zinc Complex

Freshly distilled acetylacetone (26.0312 g, 260 mmol) was dissolved in 350 mL anhydrous ethanol. Over a period of 60 minutes, 55.342 g 3-aminopropyltriethoxysilane was added dropwise to the stirred solution at room temperature. The mixture was heated overnight under reflux so as to ensure that the reaction was complete. The progress of the reaction was monitored by way of GC-MS. The solvent and the excess acetylacetone were then removed at reduced pressure. The residue was distilled at 10$^{-3}$ mbar and 130° C., wherein the product C was obtained in the form of a slightly yellowish liquid (yield 67 to 75%), which was characterized by way of $^1$H, $^{13}$C, $^{13}$C-DEPT and $^{29}$Si-NMR, elemental analysis, IR spectroscopy, and GC-MS.

Diethyl zinc was used as a 1 M solution in hexane. Toluene was dried over sodium/benzophenone and distilled under inert conditions.

In an argon atmosphere and in the absence of water, product C (9.104 g, 30 mmol) was weighed in a Schlenk tube and dissolved in 100 mL dried toluene. 15 mL of a 1 M diethyl zinc solution in hexane was added over 15 minutes at room temperature. After the addition was made, the solution was heated for 1 hour under reflux. The progress of the reaction can be tracked based on the ethane gas that develops using a gas bubble counter. The reaction is complete when ethane gas can no longer be observed. After cooling, the solvent was removed at reduced pressure, and the product was dried at 120° C. under high vacuum at $10^{-3}$ mbar. The product was obtained in the form of a slightly yellowish liquid in a yield of approximately 80% and characterized by way of $^1$H, $^{13}$C, $^{13}$C-DEPT and $^{29}$Si-NMR, elemental analysis, and IR spectroscopy.

Example 2: Production of a Zinc-Complex-Catalyzed Vinyldimethoxysilyl-Terminated Polydimethylsiloxane A 1.5-L mixer, equipped with a mechanical stirrer, heating/cooling option and a thermometer, was loaded with 5.4 mmol of a α,ω-hydroxyl-terminated polydimethylsiloxane (viscosity: 80,000 mPas). The liquid was heated to 50° C. and degassed with nitrogen. Thereafter, 0.17 mmol of the zinc catalyst from Example 1 was added. After stirring for 3 minutes, 142.6 mmol vinyltrimethoxysilane was added. The mixture was kept under nitrogen for 30 minutes at 50° C. and then degassed under vacuum for several minutes at 50° C. to remove all volatile components and obtain vinyldimethoxysilyl-terminated polydimethylsiloxane.

Example 3 (Comparative Example): Production of a Lithium-Methanolate-Catalyzed Vinyldimethoxysilyl-terminated Polydimethylsiloxane A 1.5-L mixer, equipped with a mechanical stirrer, heating/cooling option and a thermometer, was loaded with 5.4 mmol of a α,ω-hydroxyl-terminated polydimethylsiloxane (viscosity: 80,000 mPas). The liquid was heated to 50° C. and degassed with nitrogen. Thereafter, 2.7 mmol lithium methanolate was added. After stirring for 3 minutes, 142.6 mmol vinyltrimethoxysilane was added. The mixture was kept under nitrogen for 30 minutes at 50° C. and then degassed under vacuum for several minutes at 50° C. to remove all volatile components and obtain vinyldimethoxysilyl-terminated polydimethylsiloxane.

Example 4 (Comparative Example): Production of a Stopped Lithium-Methanolate-Catalyzed Vinyldimethoxysilyl-terminated Polydimethylsiloxane A 1.5-L mixer, equipped with a mechanical stirrer, heating/cooling option and a thermometer, was loaded with 5.4 mmol of a α,ω-hydroxyl-terminated polydimethylsiloxane (viscosity: 80,000 mPas). The liquid was heated to 50° C. and degassed with nitrogen. Thereafter, 2.7 mmol lithium methanolate was added. After stirring for 3 minutes, 142.6 mmol vinyltrimethoxysilane was added. The mixture was kept under nitrogen for 30 minutes at 50° C. The catalyst was then inactivated by using dry ice, and thereafter the mixture was degassed under vacuum for several minutes at 50° C. to remove all volatile components and obtain vinyldimethoxysilyl-terminated polydimethylsiloxane.

Example 5: Stability Experiment

To test the stability of the prepolymer from Examples 2 to 4, the viscosity of the capped polymer was determined at room temperature and at 70° C. over the time period. The results are shown in Table 1.

TABLE 1

Viscosity measurements (in mPas)

| Weeks | Example 2 | | Example 3 | | Example 4 | |
|---|---|---|---|---|---|---|
| | Room temperature | 70° C. | Room temperature | 70° C. | Room temperature | 70° C. |
| 1 | 76,200 | 70,000 | 82,800 | 30,000 | 55,600 | 50,600 |
| 4 | 75,300 | 61,200 | 53,200 | 7,000 | 57,200 | 32,600 |
| 6 | 74,600 | 55,000 | 49,200 | 5,400 | 57,000 | 29,400 |

Example 6: Curable Silicone Composition

The mixtures from Examples 2 to 4 were used to formulate a curable silicone composition according to Table 2.

TABLE 2

| Component | % by weight |
|---|---|
| Prepolymer | 37 |
| Plasticizer (100 mPas) | 11 |
| Fumed silica | 5.5 |
| Coated chalk (Omya BLP3) | 42 |
| Vulcanization catalyst (tetra-n-butyl-titanate) | 1.5 |
| Vinyltrimethoxysilane (desiccant) | 3 |

The produced formulations were analyzed with respect to curing speed, skin formation time, hardness, extensibility and strain. All tests were carried out for the freshly formulated silicone, and after 3 and 6 weeks of aging at 40° C./80% humidity, or 50° C. The results are shown in Table 3.

TABLE 3

Mechanical properties

| | Formulation comprising prepolymer from Example 2 | Formulation comprising prepolymer from Example 3 | Formulation comprising prepolymer from Example 4 |
|---|---|---|---|
| Shore A 1 d/7 d | | | |
| Fresh | 30/35 | 31/31 | 28/35 |
| 3 weeks of aging | 25/37 | 7/32 | 7/34 |
| 6 weeks of aging | 15/25 | 4/15 | 7/16 |
| Skin formation time (min) | | | |
| Fresh | 10 | 8 | 10 |
| 3 weeks of aging | 15 | 37 | 26 |
| 6 weeks of aging | 15 | 20 | 15 |
| Through-curing volume (mm/24 h) | | | |
| Fresh | 1.8 | 1.6 | 1.5 |
| 3 weeks of aging | 1.5 | 2.9 | 2.1 |
| 6 weeks of aging | 1.3 | 3.3 | 2.8 |
| F-max (elongation; N/mm$^2$) | | | |
| Fresh | 1.7 | 1.3 | 1.5 |
| 3 weeks of aging | 1.4 | 1.0 | 1.4 |
| 6 weeks of aging | 1.2 | 0.7 | 1.0 |
| Elongation at break (%) | | | |
| Fresh | 503 | 405 | 483 |
| 3 weeks of aging | 509 | 493 | 570 |
| 6 weeks of aging | 519 | 462 | 496 |

Measuring the Skin Formation Time

The skin formation time was determined in a normal climate (23+/−2° C., relative humidity 50+/−5%). The temperature of the sealant must be 23+/−2° C., and the sealant must be pre-stored in the laboratory for at least 24 hours. The sealant is applied to a sheet of paper and, using a spatula, drawn out to form a skin (thickness approximately 2 mm, width approximately 7 cm). Immediately start the stop watch. Lightly touch the surface with the fingertip in intervals, and pull the finger away again; push on the surface so strongly that an impression remains on the surface when the skin formation time has been reached. The skin formation time has been reached when sealing compound no longer adheres to the fingertip. The skin formation time is indicated in minutes.

Measuring the Shore A Hardness

The measurement is carried out according to ISO 868.

Measuring the Depth of Cure

A sealant bead having a height of 10 mm (+/−1 mm) and a width of 20 mm (+/−2 mm) is applied to a plastic map sheet using an appropriate spatula. After storage for 24 hours in a normal climate (23+/−2° C., relative humidity 50+/−5%), a piece is cut from the bead, and the thickness of the cured layer is measured by way of a sliding caliper. The depth of cure is indicated in [mm/24 h].

Measuring the Mechanical Properties (Tensile Test)

The tensile test is used to determine tensile strength, elongation at break and stress-strain values (modulus of elasticity) based on DIN 53504.

Deviation from standard: Shouldered test bars having the following dimensions were used as samples: Thickness: 2+/−0.2 mm; width of the web: 10+/−0.5 mm; length of the web: approximately 45 mm; total length: 9 cm. Testing was carried out in a normal climate (23+/−2° C., 50+/−5% relative humidity). The test was carried out after 7 days of curing.

Execution: A 2-mm-thick film is drawn out of the sealing compound. The film is stored for 7 days in a normal climate, and then the shouldered test bars are stamped out. For each determination, three shouldered test bars must be produced. The test is to be carried out in a normal climate. The specimens must first be adapted (which is to say stored) to the test temperature for at least 20 minutes. Prior to the measurement, the thickness of the samples must be measured in at least 3 locations at room temperature using a sliding caliper, which is to say preferably the ends and the center of the shouldered test bars must be measured within the initial measuring length. In the case of elastic materials, it is additionally recommended to measure transversely across the web. The mean value must be entered into the measuring program. The samples must be clamped in the tensile testing machine so that the longitudinal axis coincides with the mechanical axis of the tensile testing machine, and a preferably large surface area of the bar heads is captured, without clamping the web. Using an advancement speed of 50 mm/min, the shouldered test bar is pretensioned to <0.1 MPa. Thereafter, the force-elongation change curve is recorded at an advancement speed of 50 mm/min. Evaluation: The following values are to be derived from the measurement: tensile strength in [N/mm$^2$], elongation at break in [%] and modulus of elasticity at 100% strain in [N/mm$^2$].

The results show that significantly higher and more stable Shore A hardnesses can be achieved by way of the catalyst according to the invention, as well as mechanical properties that are comparable to the lithium-based compounds prior to and after aging, and more stable skin formation times.

What is claimed is:

1. A zinc complex of formula (1),

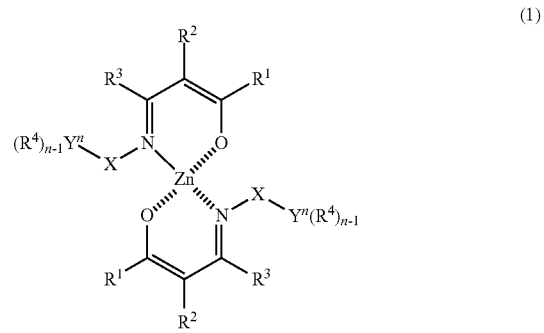

wherein each $R^1$, $R^2$ and $R^3$, independently of one another, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
—$OR^5$, —$SR^5$, —$N(R^5)_2$, —$Si(R^5)_3$ or —$P(R^5)_3$; or $R^1$ and $R^2$, or $R^2$ and $R^3$, together with the carbon atoms to which they are bound, form a 5- to 8-membered substituted or unsubstituted cycloaliphatic, heteroalicyclic aryl or heteroaryl ring;

each X, independently, denotes a divalent functional group, which is selected from,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group;

each $Y^n$, independently, denotes Si, Ge, N, P, S, wherein n denotes the oxidation state or the valence;

each $R^4$, independently, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
—$OR^5$, —$SR^5$, —$N(R^5)_2$, —$Si(R^5)_3$ or —$P(R^5)_3$; or
two $R^4$, together with $Y^n$, form a 5- to 8-membered substituted or unsubstituted cycloaliphatic, heteroalicyclic aryl or heteroaryl ring, with the proviso that
when $Y^n$ is S, $R^4$ is not —$SR^5$ or —$N(R^5)_2$,
when $Y^n$ is Si or P, $R^4$ is not $Si(R^5)_3$ or —$P(R^5)_3$;

each $R^5$, independently, denotes
hydrogen,
a substituted or unsubstituted alkyl, alkenyl or alkynyl functional group,
a substituted or unsubstituted cycloaliphatic functional group or aryl functional group, or
a substituted or unsubstituted heteroalicyclic functional group or heteroaryl functional group; or each $Y^n$, independently, denotes C, wherein n denotes the oxidation state or the valence;

each $R^4$, independently, denotes,
hydrogen,
a substituted or unsubstituted alkenyl or alkynyl functional group,
a substituted or unsubstituted cycloaliphatic functional group or aryl functional group,
a substituted or unsubstituted heteroalicyclic functional group or heteroaryl functional group,
$-OR^5$, $-SR^5$, $-N(R^5)_2$, $-Si(R^5)_3$ or $-P(R^5)_3$; or
two $R^4$, together with $Y^n$, form a 5- to 8-membered substituted or unsubstituted cycloaliphatic, heteroalicyclic aryl or heteroaryl ring, with the proviso that
when $Y^n$ is S, $R^4$ is not $-SR^5$ or $-N(R^5)_2$,
when $Y^n$ is Si or P, $R^4$ is not $Si(R^5)_3$ or $-P(R^5)_3$;
each $R^5$, independently, denotes
hydrogen,
a substituted or unsubstituted alkyl, alkenyl or alkynyl functional group,
a substituted or unsubstituted cycloaliphatic functional group or aryl functional group, or
a substituted or unsubstituted heteroalicyclic functional group or heteroaryl functional group; and
each n, independently, is an integer from 1 to 4.

2. The zinc complex according to claim 1, wherein $R^1$, $R^2$ and $R^3$ are selected from hydrogen or a substituted or unsubstituted alkyl functional group.

3. The zinc complex according to claim 1, wherein $R^1$ and $R^3$ are methyl and $R^2$ is hydrogen.

4. The zinc complex according to claim 1, wherein X is an alkyl functional group of formula $-(CH_2)_p-$, wherein p is an integer from 1 to 6.

5. The zinc complex according to claim 1, wherein $Y^n$ is Si.

6. The zinc complex according to claim 1, wherein $Y^n$ is Si; $R^4$ is $-OR^5$, and $R^5$ is $C_{1-4}$ alkyl.

7. The zinc complex according to claim 1, wherein $Y^n$ is Si; $R^4$ is $-OR^5$, and $R^5$ is methyl or ethyl.

8. A composition comprising at least one zinc complex according to claim 1.

9. A catalyst that can catalyze the condensation reaction of organosilicon compounds comprising the zinc complex according to claim 1.

10. A method for producing a curable polymer having at least one terminal functional group bound to a silicon atom, comprising:
providing a catalyst comprising at least one zinc complex of formula (1),

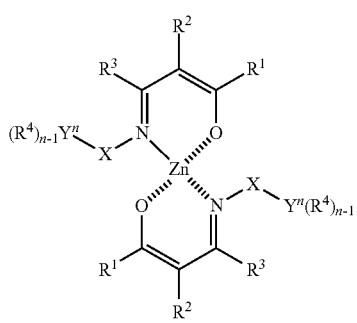

(1)

wherein
each $R^1$, $R^2$ and $R^3$, independently of one another, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
$-OR^5$, $-SR^5$, $-N(R^5)_2$, $-Si(R^5)_3$ or $-P(R^5)_3$; or
$R^1$ and $R^2$, or $R^2$ and $R^3$, together with the carbon atoms to which they are bound, form a 5- to 8-membered substituted or unsubstituted cycloaliphatic, heteroalicyclic aryl or heteroaryl ring;
each X, independently, denotes a divalent functional group, which is selected from
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group;
each $Y^n$, independently, denotes Si, Ge, N, P, O, S, wherein n denotes the oxidation state or the valence;
each $R^4$, independently, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
$-OR^5$, $-SR^5$, $-N(R^5)_2$, $-Si(R^5)_3$ or $-P(R^5)_3$; or
two $R^4$, together with $Y^n$, form a 5- to 8-membered substituted or unsubstituted cycloaliphatic, heteroalicyclic aryl or heteroaryl ring, with the proviso that
when $Y^n$ is O or S, $R^4$ is not $-OR^5$, $-SR^5$ or $-N(R^5)_2$,
when $Y^n$ is Si or P, $R^4$ is not $Si(R^5)_3$ or $-P(R^5)_3$;
each $R^5$, independently, denotes
hydrogen,
a substituted or unsubstituted alkyl, alkenyl or alkynyl functional group,
a substituted or unsubstituted cycloaliphatic functional group or aryl functional group, or
a substituted or unsubstituted heteroalicyclic functional group or heteroaryl functional group; or
each $Y^n$, independently, denotes C, wherein n denotes the oxidation state or the valence;
each $R^4$, independently, denotes,
hydrogen,
a substituted or unsubstituted alkenyl or alkynyl functional group,
a substituted or unsubstituted cycloaliphatic functional group or aryl functional group,
a substituted or unsubstituted heteroalicyclic functional group or heteroaryl functional group,
$-OR^5$, $-SR^5$, $-N(R^5)_2$, $-Si(R^5)_3$ or $-P(R^5)_3$; or
two $R^4$, together with $Y^n$, form a 5- to 8-membered substituted or unsubstituted cycloaliphatic, heteroalicyclic aryl or heteroaryl ring, with the proviso that
when $Y^n$ is O or S, $R^4$ is not $-OR^5$, $-SR^5$ or $-N(R^5)_2$,
when $Y^n$ is Si or P, $R^4$ is not $Si(R^5)_3$ or $-P(R^5)_3$;
each $R^5$, independently, denotes
hydrogen,
a substituted or unsubstituted alkyl, alkenyl or alkynyl functional group,
a substituted or unsubstituted cycloaliphatic functional group or aryl functional group, or
a substituted or unsubstituted heteroalicyclic functional group or heteroaryl functional group; and
each n, independently, is an integer from 1 to 4; and reacting a silanol-terminated polymer in the presence of the catalyst.

11. The method of claim 10, wherein:
the silanol-terminated polymer is a polydiorganosiloxane and is reacted with at least one compound of formula (2)

wherein
each $R^{10}$ denotes a hydrocarbon functional group having 1 to 20 carbon atoms, or a triorganosiloxane group of formula —O—Si($R^{13}$)$_3$, wherein each $R^{13}$, independently, denotes a hydrocarbon functional group having 1 to 20 carbon atoms;
each $R^{11}$ denotes a functional group of formula -(L)$_n$-(F)$_o$, wherein L is a divalent or trivalent hydrocarbon functional group, which optionally comprises one or more heteroatoms, F is an unsaturated $C_{2-6}$ hydrocarbon functional group, halogen, a perfluorinated hydrocarbon functional group, glycidoxy, —NHR$^{14}$ or —O—C(O)—CR$^{15}$═CR$^{16}$R$^{17}$,
wherein $R^{14}$ is hydrogen, $C_{1-6}$ alkyl or L-NH$_2$, $R^{15}$, $R^{16}$ and $R^{17}$, independently, are hydrogen, $C_{1-6}$ alkyl or phenyl,
n is 0 or 1, and
o is 1 or 2;
each $R^{12}$, independently, comprises a hydroxy group or a hydrolyzable group;
k is 0, 1, 2 or 3;
m is 0 or 1,
wherein k+m=0, 1, 2 or 3, with the proviso that m is not 0 when k+m=3.

12. The method of claim 10, wherein L is a divalent or trivalent hydrocarbon functional group, which optionally comprises one or more oxygen atoms.

13. The method of claim 10, wherein each $R^{12}$, independently, comprises an oxime group and/or an alkoxy group.

14. The method of claim 10, wherein the catalyzed reaction is the end capping of a silanol-terminated polymer comprising at least one compound of formula (2)

wherein
each $R^5$ denotes a hydrocarbon functional group having 1 to 20 carbon atoms, or a triorganosiloxane group of formula —O—Si($R^8$)$_3$, wherein each $R^8$, independently, denotes a hydrocarbon functional group having 1 to 20 carbon atoms;
each $R^6$ denotes a functional group of formula -(L)$_n$-(F)$_o$, wherein L is a divalent or trivalent hydrocarbon functional group, which optionally comprises one or more heteroatoms, F is an unsaturated $C_{2-6}$ hydrocarbon functional group, halogen, a perfluorinated hydrocarbon functional group, —NHR$^9$ or —O—C(O)—CR$^{10}$═CR$^{11}$R$^{12}$,
wherein $R^9$ is hydrogen, $C_{1-6}$ alkyl or L-NH$_2$, $R^{10}$, $R^{11}$ and $R^{12}$, independently, are hydrogen, $C_{1-6}$ alkyl or phenyl,
n is 0 or 1, and
o is 1 or 2;
each $R^7$, independently, denotes a hydroxy group or a hydrolyzable group;
k is 0, 1, 2 or 3;
m is 0 or 1,
wherein k+m=0, 1, 2 or 3, with the proviso that m is not 0 when k+m=3.

15. The method of claim 14, wherein each $R^7$, is independently an oxime group and/or an alkoxy group.

16. A curable polymer obtained from the method according to claim 10.

17. A curable composition, comprising the curable polymer according to claim 16.

18. A zinc complex of formula (1),

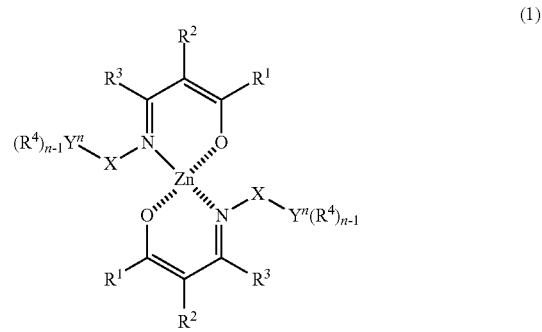

wherein
each $R^1$, $R^2$ and $R^3$, independently of one another, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
—OR$^5$, —SR$^5$, —N(R$^5$)$_2$, —Si(R$^5$)$_3$ or —P(R$^5$)$_3$; or
$R^1$ and $R^2$, or $R^2$ and $R^3$, together with the carbon atoms to which they are bound, form a 5- to 8-membered substituted or unsubstituted cycloaliphatic, heteroalicyclic aryl or heteroaryl ring;
each X, independently, denotes a divalent functional group, which is selected from,
a substituted or unsubstituted alkenyl or alkynyl functional group,
a substituted or unsubstituted cycloaliphatic functional group or aryl functional group,
a substituted or unsubstituted heteroalicyclic functional group or heteroaryl functional group;
each Y$^n$, independently, denotes C, Si, Ge, N, P, O, S, wherein n denotes the oxidation state or the valence;
each $R^4$, independently, denotes,
hydrogen,
a substituted or unsubstituted alkyl, alkenyl or alkynyl functional group,
a substituted or unsubstituted cycloaliphatic functional group or aryl functional group,
a substituted or unsubstituted heteroalicyclic functional group or heteroaryl functional group,
—OR$^5$, —SR$^5$, —N(R$^5$)$_2$, —Si(R$^5$)$_3$ or —P(R$^5$)$_3$; or
two $R^4$, together with Y$^n$, form a 5- to 8-membered substituted or unsubstituted cycloaliphatic, heteroalicyclic aryl or heteroaryl ring, with the proviso that
when Y$^n$ is O or S, $R^4$ is not —OR$^5$, —SR$^5$ or —N(R$^5$)$_2$,
when Y$^n$ is Si or P, $R^4$ is not Si(R$^5$)$_3$ or —P(R$^5$)$_3$;
each $R^5$, independently, denotes
hydrogen,
a substituted or unsubstituted alkyl, alkenyl or alkynyl functional group, a substituted or unsubstituted cycloaliphatic functional group or aryl functional group, or
a substituted or unsubstituted heteroalicyclic functional group or heteroaryl functional group; and
each n, independently, is an integer from 1 to 4.

* * * * *